United States Patent [19]

Varrichio et al.

[11] Patent Number: 4,553,548
[45] Date of Patent: Nov. 19, 1985

[54] INTERROGATOR FOR MUSCLE STIMULATOR

[75] Inventors: Anthony J. Varrichio; Pat L. Gordon, both of Austin, Tex.

[73] Assignee: Neuromedics, Inc., Coute, Tex.

[21] Appl. No.: 524,851

[22] Filed: Aug. 19, 1983

[51] Int. Cl.[4] .............................................. A61N 1/00
[52] U.S. Cl. .............................. 128/421; 128/419 PT
[58] Field of Search ........ 128/419 D, 419 PG, 419 F, 128/419 PT, 421-423; 368/10, 107, 9, 120; 377/15, 16, 19, 20, 26, 38, 41, 51, 107

[56] References Cited

U.S. PATENT DOCUMENTS

| | | | |
|---|---|---|---|
| 3,946,210 | 3/1976 | Fleischer | 377/107 |
| 4,026,301 | 5/1977 | Friedman et al. | 128/421 |
| 4,114,628 | 9/1978 | Rizk | 128/419 PT |
| 4,315,503 | 2/1982 | Ryaby et al. | 128/419 F |
| 4,392,496 | 7/1983 | Stanton | 128/423 W |
| 4,459,988 | 7/1984 | Dugot | 128/419 F |
| 4,467,433 | 8/1984 | Claassen et al. | 377/19 |

Primary Examiner—William E. Kamm
Assistant Examiner—Mitchell J. Shein
Attorney, Agent, or Firm—Fitch, Even, Tabin & Flannery

[57] ABSTRACT

An interrogator for remotely interrogating an internal counter of a scoliosis treatment device. An internal counter of the treatment device is incremented for those periods of time in which the treatment level of the device is in excess of a compliance level. The interrogator communicates with the internal counter by means of two serial data lines. On one data line the interrogator generates a clock signal to the internal counter for incrementing the device and on the other data line the interrogator receives a pulse indicating the internal counter has overflowed. By incrementing the internal counter through a full cycle of its maximum count the counter will retain the count present when it is interrogated. Additionally, by counting the number of clock counts comprising the period from the overflow signal to the end of a full cycle a duplication of the count in the remote internal counter can be stored in the interrogator and subsequently displayed.

25 Claims, 16 Drawing Figures

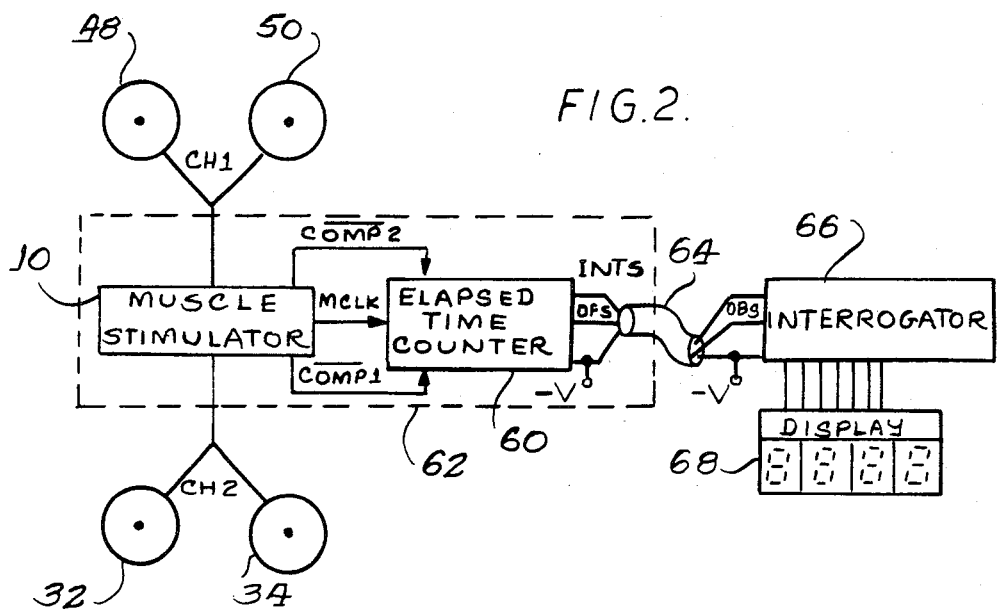
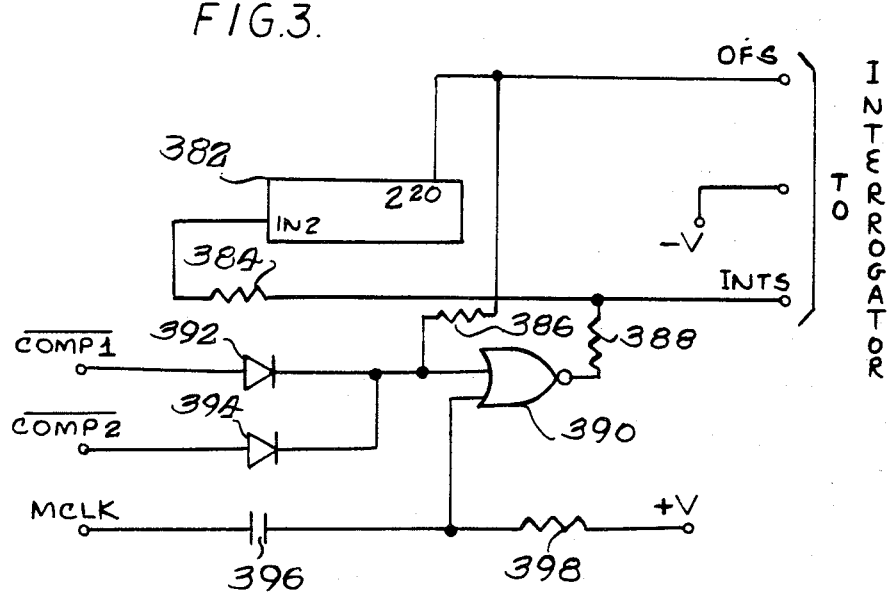

① MEDIAL (PARASPINAL MUSCLE AREA)

② INTERMEDIATE

③ LATERAL (AREA OF THE POSTERIOR AXILLARY LINE)

INTERROGATOR FOR MUSCLE STIMULATOR

The invention pertains generally to a pulse generation apparatus used for muscle stimulation and is more particularly directed to an interrogator for such muscle stimulators which are used in the treatment of Scoliosis and other related spinal deformities.

In the commonly assigned copending application Ser. No. 524,926, entitled "Muscle Stimulator" filed in the names of Anthony John Varrichio and Pat LaMar Gordon on Aug. 19, 1983, there is described a muscle stimulator for use in the treatment of Scoliosis and other related spinal deformities. The disclosure of Varrichio, et al. is hereby expressly incorporated by reference herein.

The reference includes a means for sensing compliance with a therapeutic level of the treatment described therein. The compliance sensing means is implemented as a comparator generating a first output level if the intensity level setting of the stimulation is greater than a compliance level and a second output level if the intensity level is less than the compliance level.

The compliance signal is thereafter used to visually indicate to the patient when the treatment level is in excess of the compliance level. The indication is useful in setting the intensity level of the treatment device such that the level can be adjusted upwardly as the tolerance level increases to the therapeutic level without overtreatment and unnecessary discomfort. The compliance indication is additionally useful in allowing the patient to record the period of time during which a therapeutic level of stimulation is applied.

However, the clinician who is supervising a treatment regime has little way of confirming how concientiously the patient is adhering to the treatment schedule set out. Other than the times during an office visit, the clinician has little control over the course of the treatments. At these brief interviews the clinician must interrpret the data given him by the patient as to compliance with the treatment regime and compare that with the actual progress being made. From the comparison he will attempt to make course corrections that will increase the progress of treatment and reduce the overall duration of the regime.

It is apparent that to make advantageous course corrections and monitor the progress of the treatment, accurate records be kept as to the time duration of the individual treatments and the intensity level of each. The patients consider it a substantial burden to keep the treatment records and thus, for this and other reasons, the records given to the clinician are many times incomplete, inaccurate, or even missing altogether. Even for those patients who are diligent in keeping records for session, the clinician understands there is some inaccuracy because the record is really only an estimate of the time the treatment level was in excess of the therapeutic level.

SUMMARY OF THE INVENTION

The invention overcomes these problems and provides a means for accurately accummulating the amount of time that the intensity level of a treatment device, such as a muscle stimulator, is in excess of a therapeutic level. The invention additionally provides means for interrogating the accumulator, storing, and displaying the accumulated total time.

By having an accurate record of the treatment time of a patient at a therapeutic level, a clinician using a muscle stimulator in the treatment of scoliosis or a related disease can make significantly better course corrections than one that has questionable data. Further, if a clinician has the patient keep substantially accurate records of a treatment regime, the data supplied by the invention can be used as a cross check to ensure treatment compliance.

In a preferred embodiment, the invention comprises a counter contained internally within a muscle stimulator or treatment device to store counts of a clock waveform having a periodic rate. The clock waveform is enabled to the counter causing a count accumulation during the presence of a compliance signal indicating that the intensity level of the treatment device is in excess of a therapeutic level. The clock waveform is of a constant frequency and therefore causes a time count accumulation in units of the waveform period.

The invention further comprises a means and method for interrogating the time accumulation in the internal counter. The interrogator comprises a means for clocking the internal counter for a full cycle of its maximum count i.e. from zero to overflow, means for receiving an overflow signal from the internal counter, and means for counting from the overflow to the end of a cycle. In this manner the counting means and the internal counter will both initiate counting at the same count (zero), and accumulate counts to the same count (that which was previously stored in the internal counter). A duplication of the count stored in the internal counter is thereby transferred to the counting means.

Additionally, in response to a reset signal, the invention includes means to terminate the clocking cycle upon the receipt of the overflow signal. This provides a means for clearing the internal counter such that a new treatment record can be started.

These, and other objects, features, and aspects of the invention will be better described and more fully understood if a reading of the following detailed description is undertaken in conjunction with the appended drawings wherein:

BRIEF DESCRIPTION OF THE DRAWINGS

FIG. 2 is a detailed block diagram of a muscle stimulator system including the muscle stimulator illustrated in FIG. 1, an elapsed time counter for accumulating the time of treatment at a therapeutic level, and an interrogator for reading, storing, and displaying the accumulation;

FIG. 3 is a detailed electrical schematic diagram of the elapsed time counter illustrated in FIG. 2;

DETAILED DESCRIPTION OF THE PREFERRED EMBODIMENT

Figure 1:
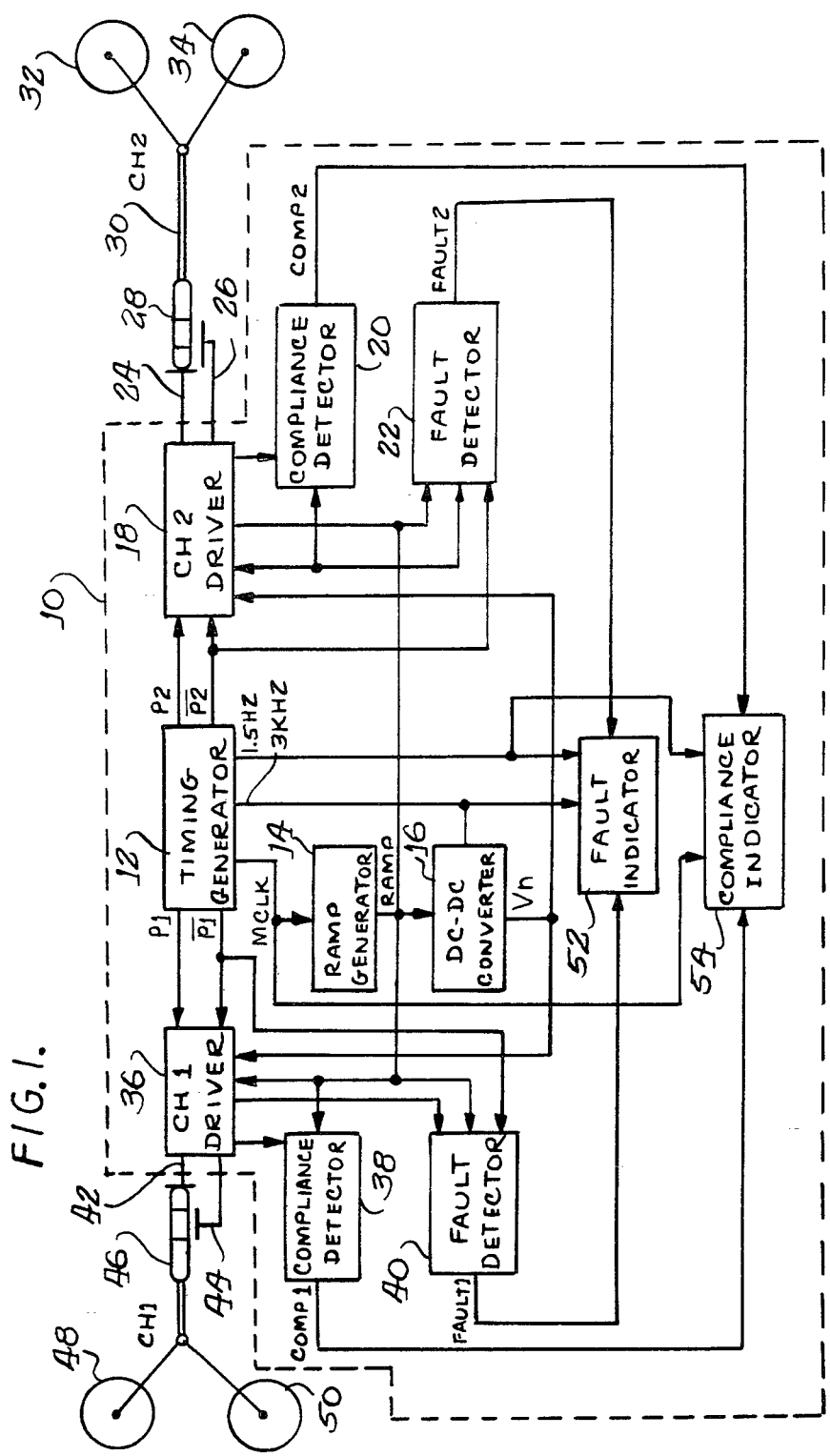
FIG. 1 is a detailed block diagram of a muscle stimulator used for the treatment of Scoliosis and other related spinal deformities.

In FIG. 1 there is shown a detailed block diagram of a dual channel muscle stimulator or therapy device 10 which can advantageously be used with the invention. Generally, the muscle stimulator is contemplated as a portable hand held device which can be conveniently used in the home setting of the patient. The device is usually battery powered to provide greater flexibility in its use. The packaging and power supply of the device have not been illustrated since it is not relevant to a description of the invention, but it should be noted that the circuitry described will be compatible with this context.

The muscle stimulator 10 develops burst of pulses having "on" and "off" periods from the outputs of two channel driver circuits 18, 36. The channel 1 driver circuit 36 for example generates pulses to terminals 42, 44 of an input jack into which a plug 46 connected to the lead terminals 27 of an electrode pair 48, 50 is inserted. The electrodes 48, 50 are positioned on a patient in a manner which will be more fully described with reference to the procedure for the treatment of deformity. Similarly, the channel 2 driver circuit 18 is connected to electrodes 32, 34 via input jack terminals 24, 26; plug 28, and lead terminals 30.

Each channel driver transforms a logic level pulse train or timing signal generated from timing generator 12 into a higher level output pulse train of a predetermined pulse width and with a constant current level. The channel 1 driver circuit 36 transforms the pulse train P1, $\overline{P1}$ into a higher level waveshape and the channel 2 driver circuit 18 transforms the pulse train P2, $\overline{P2}$ into a higher level waveshape. The step up in power is accomplished by providing each channel driver circuit 18, 36 with a high DC potential Vh. Basically, the high potential Vh is applied to the electrodes during the presence of a timing pulse and the current of each resulting high level pulse controlled to a predetermined value.

The high DC potential Vh is obtained from a DC-DC converter 16 which transforms battery potential into a supply potential of approximat 180 V DC at its peak. The converter 16 utilizes a 3 KHZ signal input from the timing generator 12 in the voltage step up process. The wave shape of the attenuated high voltage potential Vh is generated as always greater than or equal to the waveshape of an input signal RAMP generated from a ramp generator 14.

The DC-DC converter 16 thus acts as a means of amplifying or stepping up the power and voltage of the output of the ramp generator 14. The trapezoidal waveform period is based on the period of a square wave master clock signal MCLK input to the ramp generator 14 from the timing generator 12. The trapezoid is generated by linearly ramping from a zero level to a base level at one transition of the MCLK signal and then by linearly ramping from the base level to a zero level at the other transition of the master clock signal MCLK.

Associated with each driver circuit, for example channel 1 circuit 36, is a compliance detector 38 and a fault detector 40. The compliance circuit 38 receives the signal RAMP and a signal ILS which is an indication of the current intensity level of the driver circuit 36. The RAMP signal is used to generate a compliance current level which is set during a visit to the clinician. These levels are compared and a compliance signal $\overline{COMP1}$ is generated when the intensity level of the pulses is greater than the level set by the clinician. A compliance detector 20 is connected and operates similarly to the compliance detector 38 to generate the signal $\overline{COMP2}$ for channel 2 compliance. The compliance signals $\overline{COMP1}$, $\overline{COMP2}$ are received by a compliance indicator circuit 54 which is adapted to visually indicate whether compliance or noncompliance is taking place with respect to the intensity setting for each channel. The signal MCLK is used by the compliance indicator 54 to differentiate between the two separate channels and the 1.5 HZ signal used to drive an indicating device.

The detailed circuit operation and waveforms for the muscle stimulator illustrated in FIG. 1 are more fully set forth in the referenced copending application to Varrichio, et al.

The muscle stimulator system according to the invention is set out more clearly in block diagram form in FIG. 2. The dual channel stimulator 10 previously described in FIG. 1 has contained within the same physical case 62 an elapsed time counter 60. The elapsed time counter receives the compliance signals $\overline{COMP1}$, $\overline{COMP2}$, and the master clock signal MCLK. When the compliance signals are present, the elapsed time counter will be incremented at the rate of the master clock signal MCLK. Because this signal has a predetermined frequency the count in the elapsed time counter 60 will be representative of the time the compliance signal are present. The time units of the count are equivalent to the period of the master clock signal MCLK.

Further in accordance with the invention, the elapsed time counter 60 can be read by an interrogator 66 connected remotely via a transmission line 64. The interrogator performs the interrogation by transmitting an interrogate signal INTS to the elapsed time counter 60 via the trnasmission line 64. The elapsed time counter is adapted to reply via the transmission line 64 with an overflow signal OFS. The communication interface between the interrogater and the elapsed time counter additionally includes a common connection to the negative battery voltage $-V$ for a reference. Once the interrogation has been accomplished a display 68 can be used to display the time that the muscle stimulator has been used in compliance with the treatment schedule.

Detailed circuitry comprising the elapsed time counter circuit 60 is more fully illustrated in FIG. 3 where a counter 382 is used to record cycles of the treatment device which are in excess of the compliance level. The counter 382 is incremented by a driver, NOR gate 390, which has its output connected to the clock input IN2 of the counter via resistors 384, and 388. One input of the NOR gate 390 receives the channel 1 compliance signal $\overline{COMP1}$ via diode 392 and the other diode 394. The cathodes of the diodes 392, 394 are joined to provide a wired AND function. The other input of gate 390 is connected to the junction of the serial connection of a capacitor 396 and a resistor 398 connected between the master clock signal MCLK and positive battery voltage $+V$.

When both of the compliance signal $\overline{COMP1}$, $\overline{COMP2}$ provide an enabling signal (low logic level) to the NOR gate 390 indicating that compliance with a therapeutic level is taking place on both channels, then a pulse generated by the differentiator formed by capacitor 396 and resistor 398 passes through the gate 390 and clocks the counter 382. If only one channel is being used then that is the only compliance signal necessary to enable the counter 382. If enough counts have accumulated to cause the counter 382 to overflow, as sensed by a high logic level from the $2^{20}$ output, then this bit is used as an overflow bit signal OFS for transmission to the interrogator 66. A resistor 386 feeds the OFS signal back to the input of the gate 390 such that the gate is disabled in the event of an overflow. The counter 382 is adapted to have its contents read by the external interrogator circuit 66 by having the interrogator signal INTS connected to its clock input IN2.

Figure 4:
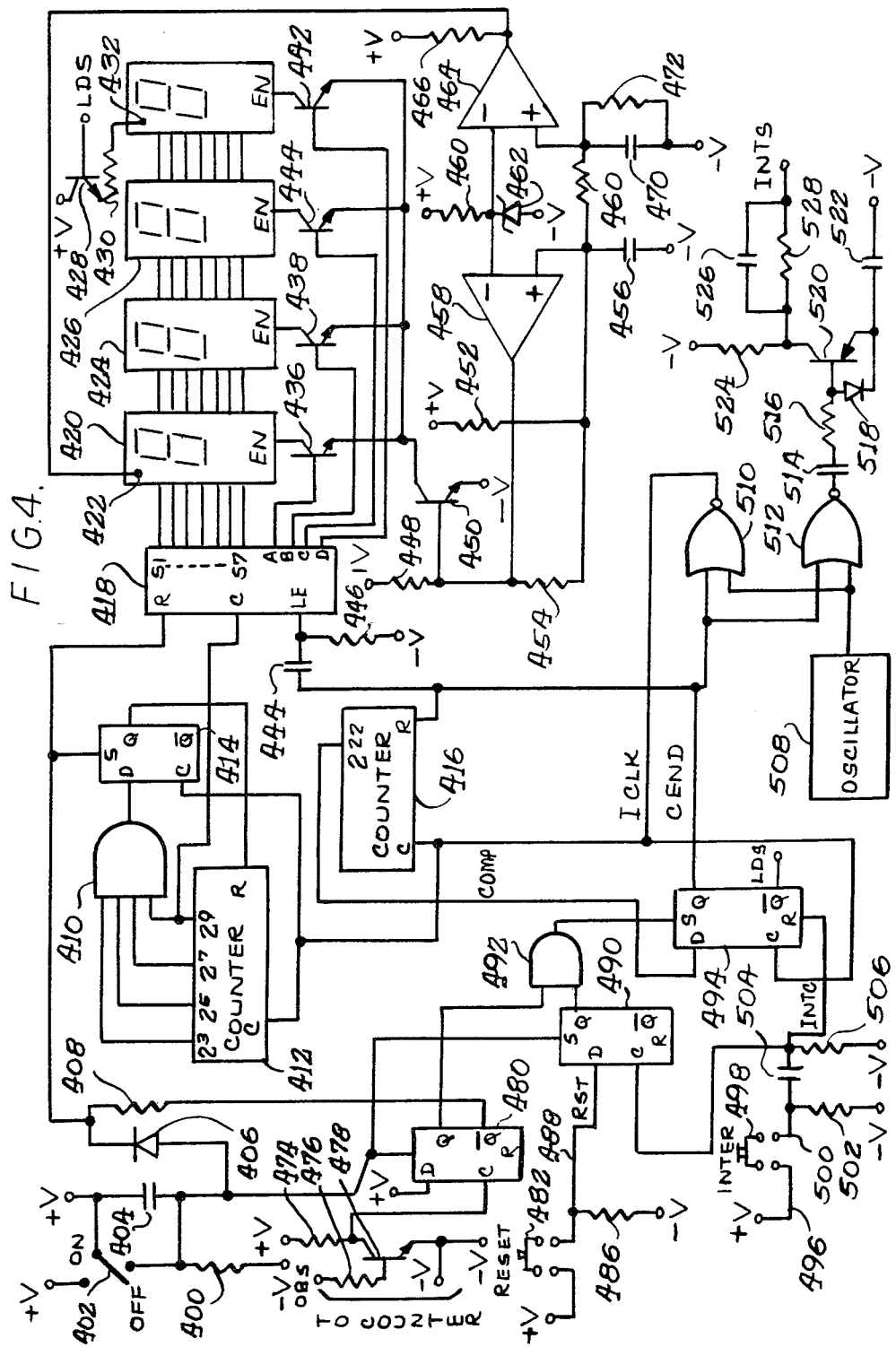
FIG. 4 is a detailed electrical schematic diagram of the interrogator illustrated in FIG. 2.

The detailed description of the interrogator circuitry will now be more fully explained with respect to FIG. 4. The interrogator includes a four digit display counter 418 which drives four seven segment displays 420, 424, 426 and 434 connected in parallel with the inputs S1-S7 of the counter. Each display 420, 424, 426, 434 is enabled by a separate NPN transistor 436, 438, 444, 442 respectively, by having the collector of the transistor connected to common cathode input EN of the display. The emitters of the transistors 436, 438, 444, 442 are commonly connected to the negative battery voltage −V via the collector emitter path of a transistor 450 while their base terminals receives enabling signals directly from selector outputs A, B, C, D respectively of the counter 418. Th four digits of an internal counter are placed output lines S1-S7 sequentially in the code of the seven segment displays. Each digit is simultaneously accompanied by an enabling output signal from one of the outputs A-D. The activation and transfer of the digits is at a frequency such that the display appears as a solid readout. The four digit contents of the display driver is refreshed by the internal counter 418 whenever the load enable input LE is activated and remains displayed until the next sequence. The internal counter of the display counter 418 is incremented by a signal applied to the clock input C of the display counter 418 and is reset by a signal applied to the reset input R of the display counter.

The display counter 418 is clocked by the $2^9$ output of a divider counter 412. The divider counter 412 has its $2^3$, $2^5$, $2^7$, and $2^9$ outputs decoded by an 410 whose output drives the D input of flip flop 414. The Q output of the flip-flop 414 is connected to the reset input R of counter 412. The clock input C of the flip flop 414 and the divider counter 412 are commonly connected to a clock line carrying the interrogator clock signal ICLK. The divider counter is incremented by the signal ICLK and generates its clock signal to the counter 418 every predetermined number of increments. The number of counts in the divider counter 412 is decoded by the AND gate 410 which provides a high level output to the D input of flip flop 414 when that number is reached. Because of the high logic level provided to the D input, the next ICLK pulse to the flip-flop 414 sets the Q output thereby resetting the divider counter 412. The divider counter thereby divides the frequency of the ICLK signal by a predetermined constant. In the present embodiment this constant is 534 which is a conversion factor to changes the ICLK pulses representing counts of the MCLK signal to hours.

A cycle counter 416 is additionally provided to determine when one full cycle of interrogation has been accomplished. The clock input C of the cycle counter 416 is driven by the signal ICLK and complete signal COMP is generated from its $2^{22}$ output. The cycle counter is twice the length of the elapsed time counter in the therapeutic device. A complete interrogation cycle is therefore a clocking from a zero condition to an overflow of the cycle counter corresponding to an analogous complete cycle for the elapsed time counter.

The cycle complete signal COMP is applied to the D input of an interrogate flip flop 494. The clock input C of the flip flop 494 receives the signal ICLK and the reset input R of the flip flop 494 receives an interrogate command INTC in the form of a pulse from a differentiator circuit and an interrogate button 498. When it is depressed the interrogate button 498 connects positive battery voltage +V through terminals 496, 500 to a capacitor 504. At one terminal the capacitor 504 is connected to the negative battery voltage −V through a resistor 502 and at the other terminal is connected to negative battery voltage −V through a resistor 506. The rising edge of the positive voltage is differentiated by the resistor-capacitor combination, 502, 504 and 506 to become a positive pulse interrogate command INTC. The interrogate command INTC is additionally applied to the clock input C of a reset flip flop 490 and to the reset input R of an overflow flip flop 480.

The reset flip flop 490 of an overflow its D input the reset signal RST. The signal RST is generated by a push button 482 connecting positive battery voltage +V via terminals 482, 484 to one terminal of a resistor 486 whose other terminal is connected to negative battery voltage −V. The Q output of the reset flip flop is connected to one input of AND gate 492 whose other input is the Q output of the overflow flip flop 480. Therefore, if the reset button is depressed and held, and subsequently an interrogate command is given, then the reset flip flop 490 is set. If the reset flip flop 490 is set at the time the overflow signal is received the cycle is terminated. The internal counter of the therapy device is thereby cleared to a zero count.

The overflow flip flop 480 records the occurance of an overflow of the elapsed time counter 60 by having its clock input connected to the OFS signal via a NPN buffer transistor 478 and its D input connected to positive battery voltage +V. The base of the transistor 478 is connected to the external transmission line via resistor 476 and its collector-emitter path connected between the clock input C of the flip flop 480 and negative battery voltage −V. A pullup resistor 474 is also provided between the collector terminal of the transistor 478 the positive battery voltage +V. When the signal is received over the transmission line flip flop 480 will set.

An initial power on reset is applied to the set inputs S of the overflow flip flop 480 and the reset flip flop 490 via a reset circuit comprising a capacitor 404, a resistor 400, and an on/off switch 402. The capacitor 404 is connected between the positive battery voltage +V and one terminal of a resistor 400 whose other terminal is connected to the negative battery voltage −V. The on/off switch 402 shorts the capacitor 404 when in the on position. The set terminals S upon power up, therefore, initially have positive battery voltage +V applied to them causing a predetermined state transition. The voltage on the capacitor 404 charges lowering the voltage at the junction of the capacitor 404 and resistor 400 thereby removing the reset.

The initial power on reset is additionally applied through diode 406 to the set input S of flip flop 414 and the reset input R of the display counter 418. In parallel with the initial power on reset to flip flop 414 and display counter 418 is a reset signal from the output $\overline{Q}$ of the overflow flip flop 480 via resistor 408.

The interrogator clock signal ICLK is generated by an oscillator 508 at a much higher frequency than the master clock signal used for incrementing the elapsed time counter. In the preferred embodiment the interrogator clock frequency is 2 MHZ. The interrogator clock signal ICLK is transmitted to the clock inputs C of the cycle counter 416, the divider counter 412, the interrogate flip flop 494, and the decoder flip flop 414 via the output of a NOR gate 510. A companion NOR gate 512 transmits the interrogator clock signal ICLK to a transmission line driver circuit via its output. The NOR gates 510, 512 are each enabled and disabled by the logic level signal CEND which is generated as by the Q output of the interrogate flip flop 494 which and is indicative of the start and end of a cycle.

The line driver circuit comprises a PNP transistor 520 connected in a inverter configuration in order to drive the transmission line between the interrogator and the elapsed time counter of the therapy device. The ICLK signal is delivered to the base of the transistor 520 via the capacitive coupling of a capacitor 514 and a resistor 516 from the output of NOR gate 512. A diode 518 is poled between the base and collector terminal of the transistor 520 to provide drive only for positive pulse transitions. A load resistor 524 is coupled to the collector terminal of the transistor to generate a driving voltage. The voltage generated between the negative battery voltage −V and the output at the collector terminal is trasmitted via the parallel connection of a capacitor 526 and a resistor 528 to the transmission line. The output of the line driver circuit at the transmission line connection is termed the interrogate signal INTS and is a buffered clock to the internal elapsed time of the muscle stimulator.

A low battery voltage protection circuit is used to alert personel utilizing the interrogator when battery voltage begins to drop below a certain point and thereafter disables the display if the voltage continues to drop. Since the display draws the largest amount of power from the batteries this feature provides protection from completely discharging the batteries and also provides a protection feature for the count stored in the elapsed time counter 60. The warning from the low battery protection circuit is provided by the output of a comparator 464. The output is connected to positive battery voltage +V through resistor 466 and additionally to the input for the decimal point 422 of display 420. When the decimal point is activated the battery voltage is safe and comparator 464 will be nonconducting.

However, when the battery voltage +V drops below a predetermined level the comparator 464 will become conducting thereby sinking current from resistor 466 and turning off the decimal point indication. The reference voltage for this operation is provided at the junction of the serial connection of a resistor 460 and a band gap reference, Zener diode 462, connected between the battery rail +V, −V. This reference voltage is input to the inverting input of the comparator 464 which has a portion of the battery voltage +V input to its noninverting input. The portion of the actual battery voltage is developed at the junction of a set of divider resistors 468, 472 connected in series with a resistor 452. A capacitor 470 is provided in parallel connection with resistor 472 to provide filtering. When the junction voltage at the noninverting input drops below the reference voltage, the comparator will begin conduction.

Similarly, a comparator 458 disables the display by comparing the reference voltage developed at the junction of the Zener 462 and resistor 460 with the voltage developed at the junction of resistor 452 and resistor 468. A capacitor 456 is connected in parallel across resistors 468, 472 to provide filtering for this voltage. When the fraction of actual battery voltage applied to the noninverting terminal of comparator 458 drops below the reference voltage, the comparator 458 will sink current away from the base of transistor 450. This action will cause a high impedance path between the transistors 436, 438, 444, and 442 which enable the displays and the neagative battery voltage −V thereby disabling the displays. Since the voltage at the junction of resistors 468, 452 is greater than the voltage at the junction of resistors 468, 472, the comparator 458 becomes conducting after the comparator 464 becomes conducting due to the battery voltage dropping.

Operationally, the clinician connects the interrogator to the therapy device via the transmission line whereby the signal INTS can be transmitted to the elapsed time counter of the device and the siqnal OFS can be received by the interrogator circuit from the device. The power is then turned on which generates the power on reset to set flip flops 480, 490 which thereafter sets flip flop 492 via AND gate 494. Further, the power on reset sets flip flop 414 to produce a clearing of counter 412 directly resets counter 418. The setting of flip flop 494 generates a high level logic signal which disables NOR gates 510 and 512, resets counter 416, and enables the display counter input LE. The interrogator is now initialized and in an idle mode such that displays 422, 424, 426, and 434 are all displaying zeros.

Figure 5:
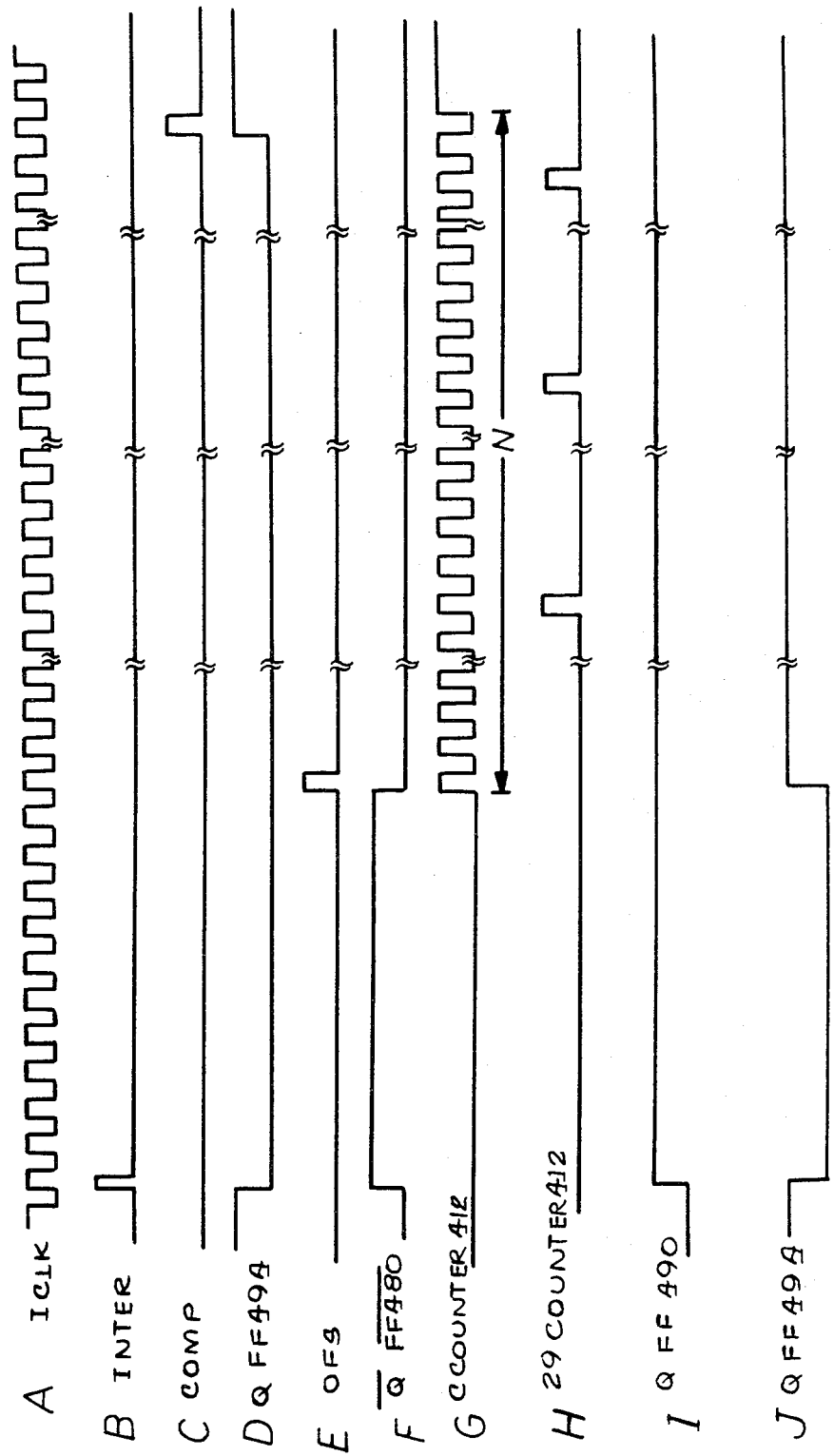
FIGS. 5A–J are pictorial representations of waveforms at various places in the circuitry illustrated in detail in FIGS. 3 and 4.

With attention now to FIG. 5, if the clinician now desires to interrogate the therapy device, the interrogate switch 498 is momentarily depressed. The interrogate command pulse figure 5B resets overflow flip flop 480 thereby holding the display counter 418 reset with its $\overline{Q}$ output. The reset flip flop 490 is cleared at this time by the interrogate command pulse clocking the low level voltage applied to it D input into its Q output. This action also resets the flip flop 494 bringing the Q output of the device to a low logic level FIG. 5D. Simultaneously, the NOR gates 410, 512 are enabled by the low level Q output to transmit the ICLK signal to the therapy device and to the cycle counter 416. The elapsed time counter of the therapy device and the cycle counter of the interrogator are thus counted or clocked together until the elapsed time counter overflows. The overflow condition causes the overflow signal OFS (FIG. 5E) to be generated over the transmissions line to set overflow flip flop 480 thereby causing its Q output to go low, FIG. 5F.

The setting of flip flop 480 removes the reset conditions on counter 412 and counter 418 allowing them now to initiate counting clock cycles FIGS. 5 G, H. The divider counter 412 counts clock cycles of the interrogator clock signal ICLK while the display counter 418 counts cycles of the divider counter. This part of the cycle continues until the cycle counter 416 overflows thereby setting the interrogator flip flop 494 via its D input FIG. 5C. The setting of flip flop 494 FIG. 5D disables the interrogator clock ICLK and counters 416 and 418 via its Q output.

The display counter 418 therefore counts from the overflow of the elapsed time counter to the end of a cycle where stored count of the elapsed time counter is reestablished. The count in the display counter is therefore a reproduction of the accumulated count in the elapsed time counter which has been converted to absolute time in hours.

If the reset flip flop 490 is set at the time of overflow (FIG. 5I), then AND gate 492 will cause the interrogate flip flop to be set disabling the signal ICLK and the counters. Thus, if the reset signal is given the internal counter of the therapy device is cleared to be able to start another record.

With reference to FIGS. 9 and 10, in carrying out the treatment process in accordance with the present invention, patients who have been diagnosed as suffering from scoliosis, lordosis, lordoscoliosis, kyphosis, or kyphoscoliosis, are initially screened to determine whether the transcutaneous electrical muscle stimulation method of treating the disease can be utilized. In carrying out the screening process, an AP (or PA) standing X-ray of the patient is taken for scoliosis, lateral standing X-ray for lordosis and kyphosis, or an AP (or PA) and lateral standing X-rays for lordoscoliosis and kyphoscoliosis, and measurements are made thereon to determine the location of the primary and compensatory curve(s) and to determine the degree of curvature of each (degrees determined by Cobb measurement method).

When the major curve to be treated is located in the thoracic area, the rib joining this apical vertebra becomes the center reference in the treatment of scoliosis, lordoscilisis and lordosis. The location of the apical is palpated from the apical vertebra so that site of stimulation is marked on the skin. Using the X-ray, the apical vertebra of the primary curve is located relative to, for example, the $C_7$ vertebra in the neck region, the latter being a vertebra which is easily located on the patient's back by touch. By counting down, then, it is possible to locate the apical vertebra on the body of the patient and when this has been done, the clinician, again by touch and sight, follows the particular rib joined to this apical vertebra out laterally from the convex side of the scoliotic curve.

The stimulating electrodes are then placed in a symmetrical fashion above and below this center reference with the negative electrode preferably being the uppermost. Initially, the distance between the electrodes may be determined by the following guideline found from a study of 40 patients: (a) a distance of 1 centimeter or less between electrode edges normally causes insufficient muscle contraction, (b) short curves of only few segments (3 to 5) or patients with short trunks normally require a distance between electrode edges of 2 to 4 centimeters, (c) based upon the most prevalent curve encountered, a distance of 5 centimeters between electrodes edges will normally suffice, (d) long single curves of patients with extremely long trunks will require a distance between electrode edges of from 6 to 11 centimeters.

Preferably, round electrodes 5 centimeters in diameter are used, but any electrode type of reasonable size and shape is acceptable. When round electrodes of 5 centimeters in diameter are utilized, the aforementioned distances between edges translate into the following distances between electrode centers: (a) 6 centimeters, (b) 7 to 9 centimeters, (c) 10 centimeters, (d) 11 to 16 centimeters.

Figure 6:
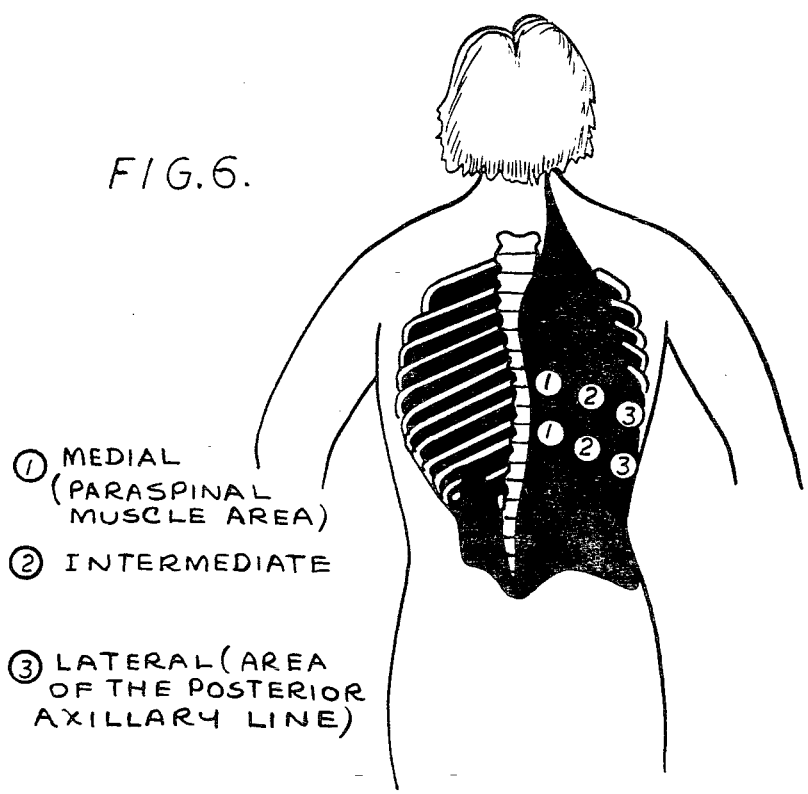
FIG. 6 is a pictorial representation of the muscle locations used in a course of treatment with the muscle stimulator illustrated in FIG. 1.
Figure 7:
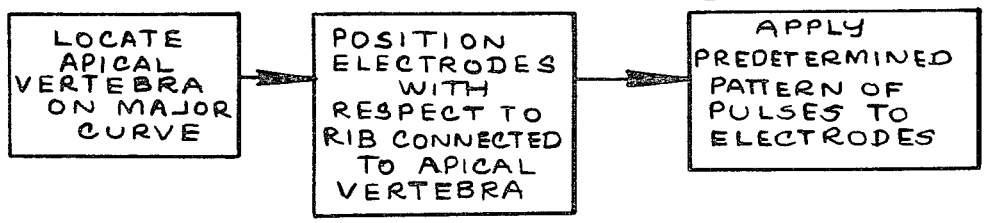
FIG. 7 is a flow diagram of the necessary steps for the treatment of scoliosis or other spinal deformities using the muscle stimulator illustrated in FIG. 1.

With the reference center and the electrode distance selected for the curve(s) to be treated, the electrodes are located symmetrically around the reference center according to the following guideline: (a) In scoliosis, the stimulation target muscles lie in the band which stretches from the edge of the paraspinal muscles to the anterior axillary line. Routinely, muscles in the area of the posterior axillary line or the mid axillary line are selected, thus note the electrode position 3, 3 of FIG. 6, for example; (b) In lordosis, the anterior midline the rectus abdominus muscle as the target is normally selected; (c) In lordoscoliosis, the stimulation target muscles lie betweem the anterior axillary line and the anterior midline; (d) In kyphosis, the posterior midline the paraspinal musculature on both sides of the spinal column as target is normally selected; (e) In kyphoscoliosis the target muscles are the paraspinal musculature around the apex of the curvature.

The locations where the electrodes are to be positioned are then marked with a semipermanent ink to facilitate later electrode placement by the patient or a member of the family. To keep the marks visible they should be touched up at regular intervals with new markings.

The electrodes themselves are preferably round discs formed from a conductive rubber material, the discs being approximately five centimeters in diameter and having a snap-type connector to facilitate joining the electrode to a conductive lead. The connector must be a radiopaque material like metal to show up in the X-rays. The lead, in turn, is coupled to the output jacks or terminals of the stimulator. The electrodes are electrically coupled to the skin either via electrically conductive gel or electrically conductive, flexible and adhesive disc shaped materials. The electrodes and skin interface media may also be integrated into one self-contained unit.

During the initial screening process, the intensity amplitude is adjusted to produce suitable muscle contractions, but without causing the patient undue distress or discomfort.

The compliance adjustment should be made by a qualified clinician only. With the unit in the Manual mode, connected to properly placed electrodes, and the maximum current adjustment knobs set to the minimum setting of approximately 10 ma, the test button is depressed allowing the stimulating pulses to ramp up to base level output. The current adjustment knobs are now slowly rotated, increasing the maximum current until the required amount of muscle contraction occurs. The test button is now released. After the current ramps down, the electrode leads are unplugged. Without moving the maximum current adjustment knobs, the test button is again depressed (the audible beeper should shound.) Both compliance adjustments are now first rotated fully counterclockwise and then advanced clockwise to the adjustment point where the compliance indicator just stops blinking and becomes continuously illuminated. The test button can now be released and the unit turned off. The proper compliance for each channel has now been prescribed and the unit is ready for patient use.

The patient is then advised to use the stimulator during an initial two-week familiarization and muscle conditioning phase, where the amplitude of stimulation is increased every day according to the increasing level of comfort. During the first week, the patient uses the stimulator during daytime only according to the following schedule in order to prevent muscle fatigue: Day 1-½ hour three separate times; Day 2-1 hour two separate times; Day 3-3 hours continuously; Day 4-4 hours; Day 5-5 hours; Day 6-6 hours; Day 7-7 hours.

On the eighth day, the beginning of the second week, stimulation application is switched to night time while the patient sleeps. If less than 8 hours of stimulation is applied at night then supplementary daytime use is required. With a presently preferred "on-off" ratio of ⅜, eight hours of stimulation corresponds to three hours that the corrective force is actually applied to the spine, the remaining time being the "off" or rest portion of the cycle. After two weeks of use, the patient will return to the clinician where an examination will be made as to whether there is any noticable skin irritation or other effects that may dictate changes of the treatment process. Possible skin irritation may be solved by the use of alternate skin interfacing materials.

Assuming that the patient does not exhibit any conditions which would preclude continued use of the method and apparatus, at the conclusion of this initial screening period, the clinician more precisely locates the electrodes based on a prone X-ray of the entire spine with electrodes attached, but with no stimulation applied. In that the patient is now accustomed to the sensation of the electrical stimulation induced muscle contractions, an additional prone X-ray of the entire spine with 70 milliamps of pulse current amplitude is taken. The X-ray is measured and compared to the non-stimulated prone reference X-ray (the patient must not move between X-rays). Improvement of the major curve and no worsening of the compensatory curve(s) must be seen. If not, further electrode adjustment is necessary.

The main objective of the treatment is not to strengthen the muscles being stimulated, but to cause asymmetrical pressures to be exerted on the affected growth zones so as to effect a biomechanical straightening of the spine. Specifically, by applying electrical stimulation to the surface of the skin proximate specific trunk muscles rather significant mechanical forces can be applied to the spine.

In utilizing the treatment method of the present invention, it is found that the amplitude of the stimulating pulses should be approximately 60-80 milliamperes, this value having been found to be a compromise between good muscle contractions and the lower pain threshold. However, as described above in connection with the preferred stimulator design, the amplitude is adjustable so that greater or lesser stimulating currents may be utilized. The daily treatment time may be in the range of from about four hours to about sixteen hours per day.

At periodic intervals, e.g., three months, the patient is expected to return to the clinician so that progress may be monitored. At the time of these visits, further X-rays may be taken to ensure that electrode placement is proper, that treatment of the major curve does not adversely affect the curvature of the compensatory curve and that the curve angle has not increased further.

The clinician additionally can make a course correction based upon the compliance of the patient with the treatment regime. The compliance level may be adjusted upwardly if the tolerance level has increased and the patient has been able to follow the course of treatment. The compliance level can also be adjusted downwardly if the patient is having trouble meeting the requirements of the regime. More or less time can be added to the treatments if this is desired for a more efficacious method of the treatment at higher or lower therapeutic levels. These records of treatment compliance by the patient can be extremely useful in developing these course corrections.

Additionally, the treatment device is then connected to the interrogator such that an accurate reading of the compliance time can be determined. From this display and the records of the patient cross checking can be accomplished. Based on all the available data, course corrections for the patient can be intelligently charted. The clinician can then reset the internal counter of the therapy device to begin a new record or continue recording on the same record depending upon the needs of the particular regime.

Upon skeletal maturity treatment is normally terminated. If the major curve has progressed more than, say five degrees, the treatment will normally be discontinued and alternate treatment initiated, but this decision is at the discretion of the clinician.

While a detailed description of the preferred embodiment has been described with specificity, it will be obvious to those skilled in the art that various modifications and changes may be made thereto without departing from the spirit and scope of the invention as is set forth in the appended claims.

What is claimed is:

1. A method for interrogating a remote counter included in a medical treatment device, wherein the count stored in the counter indicates the accumulated time of therapy for the device, including the steps of:
   generating a clocking signal;
   transmitting said clocking signal over a transmission line to the clock input of the remote counter to cause it to increment;
   generating a full cycle of clocking signal to the remote counter equivalent to its maximum number of counts thereby not changing the count stored within;
   receiving an overflow signal from the remote counter over a second transmission line indicating that the maximum count capacity of the counter has been exceeded;
   counting said clocking signal from the time said overflow signal is detected until the end of the full cycle of clocking signal thereby generating a duplication of the number of counts in the remote counter; and
   storing said duplication.

2. A method as set forther in claim 1 wherein said step of generating said clocking signal includes:
   generating said clocking signal at a substantially higher frequency than is used to increment said remote counter when used in the treatment mode.

3. A method as set forth in claim 1 which further includes the step of:
   displaying the stored duplication of the number of counts contained within said remote counter.

4. A method as set forth in claim 3 which further including the step of:
   providing an indication of a low power level when a power supply voltage drops below a first level.

5. A method as set forth in claim 1 which further includes the step of:
   disabling the step of displaying said stored duplication of the number of counts in said remote counter when the power supply voltage drops below a second level which is less than the first level.

6. A method as set forth in claim 1 which further includes the steps of:
   terminating the clocking signal upon receipt of said overflow signal in response to a reset signal thereby clearing the remote counter.

7. A method for the treatment of a condition requiring a therapeutic level of treatment comprising the steps of:

setting a reference compliance level that is sufficient to provide therapeutic treatment of the condition;

providing a treatment device with a patient settable treatment level;

comparing said reference compliance level with said treatment level;

providing a display which indicates when the treatment level is in excess of the compliance level;

treating the condition at a level that is tolerable by the patient;

accumulating the amount of time the treatment level is in excess of the compliance level;

interrogating the treatment device to determine the accumulated amount of time; and making therapeutic course corrections in the treatment in accordance with the accumulated amount of time.

8. A method as set forth in claim 7 in which the step of making course corrections further includes the step of:

increasing the compliance level after the determination of the accumulated time if the accumulated time is greater than first predetermined amount.

9. A method as set forth in claim 8 in which the step of making course corrections further includes the step of:

decreasing the compliance lever after the determination of the accummulated time if it is less than a second predetermined amount.

10. A method as set forth in claim 9 in which the step of making course corrections further includes the step of:

resetting the compliance level after the determination of the accumulated time if it is less than said first predetermined amount and greater than said second predetermined amount.

11. A method as set forth in claim 7 wherein the step of providing said treatment device includes the step of:

providing a treatment device with an internal means for accumulating the amount of time the treatment level is in excess of the reference compliance level.

12. A method as set forth in claim 11 wherein the step of interrogating the treatment device includes:

remotely interrogating the internal accumulating means with an interrogation means.

13. A muscle stimulator system comprising:

variable generating means for generating bursts of pulses of variable intensity, said pulses having alternating on and off periods for causing contractions in selected muscle groups of a patient;

means for providing a patient settable intensity signal for varying the intensity of said pulses;

means for providing a settable reference compliance signal corresponding to a desired therapeutic level;

means for comparing said intensity signal and said reference compliance signal, and for generating a compliance signal when said intensity signal is greater than said reference compliance signal;

means for indicating when said compliance signal is generated; and means for accumulating a representation of the time periods said compliance signal is generated.

14. A muscle stimulator system as set forth in claim 13 which further includes:

means for interrogating said accumulating means for said representation.

15. A muscle stimulator system as set forth in claim 14 wherein said interrogating means includes:

means for storing said representation; and means for displaying said representation.

16. A muscle stimulator system as set forth in claim 13 wherein said accumulating means includes:

an elapsed time counter having a clock input which adapted to receive a clocking signal for incrementing said counter;

said clock input receiving a periodic clocking signal having a predetermined period such that the counter counts in increments of said predetermined period, said predetermined period being related to the period of said pulse bursts; and means for enabling said periodic signal to said clock input when said compliance signal is present such that said counter counts predetermined periods that the intensity level is greater than the reference level.

17. A muscle stimulator system as set forth in claim 16 which further includes:

an interrogator, remote from said elapsed time counter, for determining the count in said counter at any particular time.

18. A muscle stimulator system as set forth in claim 17 wherein said interrogator comprises:

means for generating an interrogator clock signal;

means for transmitting said interrogator clock signal to the clock input of said elapsed time counter;

a cycle counter of the same bit length as said to elapsed time counter;

means for transmitting said interrogator clock signal to the clock input of said cycle counter;

means for detecting an overflow signal from said elapsed time counter;

means for detecting an overflow signal from said cycle counter;

means for generating an interrogator cycle wherein said elapsed time counter and said cycle counter are clocked simultaneously by said interrogate clock pulses until said cycle counter overflow is detected; and a display counter for counting said interrogator clock signal between said elapsed time overflow and said cycle counter overflow so as to generate a number equivalent to that stored in the elapsed time counter.

19. A muscle stimulator system as set forth in claim 18 which further includes:

means, responsive to the detection of a cycle counter overflow, for displaying the count stored in said display counter.

20. A muscle stimulator system as set forth in claim 19 which further includes:

a divider, disposed between said interrogator clock signal and the clock input of said display counter, for dividing the frequency of said interrogator clock signal by a predetermined number.

21. A muscle stimulator set forth in claim 20 wherein:

said predetermined number is a scaling constant transforming the elapsed time pulses into units of time.

22. A muscle stimulator system comprising:

a muscle stimulator generating variable intensity burst of pulses causing contractions in selected muscle groups of a patient;

means for varying the intensity of the pulses with an intensity level signal;

a reference intensity level signal indicative of a therapeutic intensity for said pulses;

means for generating a compliance signal indicating time periods during which said intensity level signal is greater than said reference intensity signal;

means for accumulating a representation of the time periods said compliance signal is generated, said accumulating means including an elapsed time counter having a clock input which is adapted to receive a clocking signal for incrementing said counter, said clock input receiving a periodic signal having a predetermined period such that the counter counts in increments of said predetermined period, and means for enabling said periodic signal to said clock input when said compliance signal is present such that said counter counts predetermined periods that the intensity level is greater than the reference level; and an interrogator, remote from said elapsed time counter, for determining the count in said counter at any particular time, said interrogator including means for generating an interrogator clock signal, means for transmitting said interrogator clock signal to the clock input of said elapsed time counter; a cycle counter of the same bit length as said to elapsed time counter, means for transmitting said interrogator clock signal to the clock input of said cycle counter, means for detecting an overflow signal from said elapsed time counter, means for detecting an overflow signal from said cycle counter, means for generating an interrogator cycle wherein said elapsed time counter and said cycle counter are clocked simultaneously by said interrogation clock pulses until said cycle counter overflow is detected, and a display counter for counting said interrogator clock signal between said elapsed time overflow and said cycle counter overflow so as to generate a number equivalent to that stored in the elapsed time counter.

23. A muscle stimulator system as set forth claim 22 which further includes:

means, responsive to the detection of a cycle counter overflow, for displaying the count stored in said display counter.

24. A muscle stimulator system as set forth claim 23 which further includes:

a divider, disposed between said interrogator clock signal and the clock input of said display counter, for dividing the frequency of said interrogator clock signal by a predetermined number.

25. A muscle stimulator set forth in claim 24 wherein:

said predetermined number is a scaling constant transforming the elapsed time pulses into units of time.

* * * * *